Figure 1:
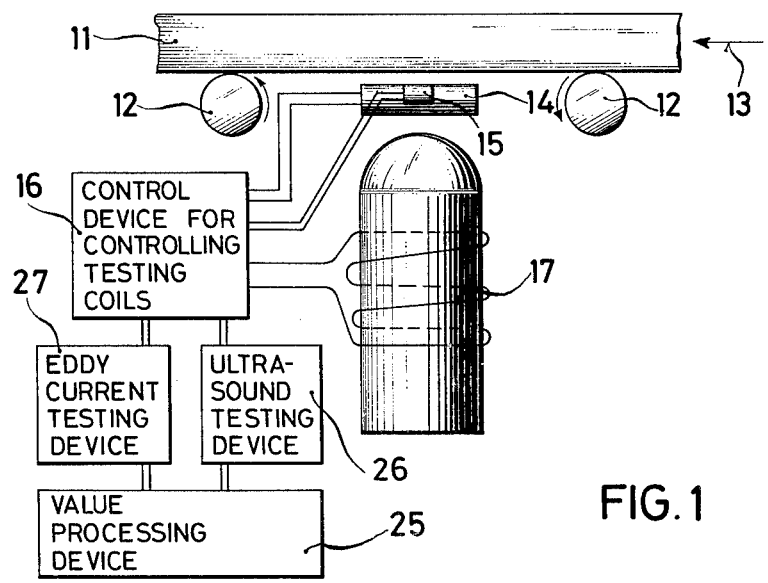

United States Patent [19]

Bottcher et al.

[11] 4,167,878

[45] Sep. 18, 1979

[54] APPARATUS FOR NON-DESTRUCTIVELY TESTING MATERIALS

[75] Inventors: Wolfgang Bottcher; Hermann-Josef Kopineck, both of Dortmund, Fed. Rep. of Germany

[73] Assignee: Hoesch Werke Aktiengesellschaft, Dortmund, Fed. Rep. of Germany

[21] Appl. No.: 851,682

[22] Filed: Nov. 15, 1977

[30] Foreign Application Priority Data

Nov. 16, 1976 [DE] Fed. Rep. of Germany ....... 2652085

[51] Int. Cl.² .......................................... G01N 29/00
[52] U.S. Cl. ..................................................... 73/601
[58] Field of Search .......................... 73/601, 643, 626

[56] References Cited

U.S. PATENT DOCUMENTS

| | | | |
|---|---|---|---|
| 3,237,446 | 3/1966 | Wood | 73/601 |
| 3,460,063 | 8/1969 | Houck et al. | 73/643 X |
| 3,583,213 | 6/1971 | Houck et al. | 73/643 X |
| 3,886,793 | 6/1975 | Cramer et al. | 73/601 X |

*Primary Examiner*—Jerry W. Myracle
*Attorney, Agent, or Firm*—Becker & Becker, Inc.

[57] ABSTRACT

An apparatus for non-destructively testing materials by ultrasound and eddy current, which includes an ultrasound material testing device operating in conformity with the electrodynamic converter principle, and also includes an eddy current material testing device. The testing coils of both testing devices are centrally arranged with regard to each other in such a way that the workpiece regions controlled by the testing coils have an at least approximately common central axis. The apparatus furthermore includes a control device which in conformity with the energization of the coil for creating the strong magnetic field for operation of the electrodynamic converter is operable briefly alternately respectively to turn-on and turn-off the respective testing coil of the ultrasound and eddy current material testing device.

9 Claims, 4 Drawing Figures

APPARATUS FOR NON-DESTRUCTIVELY TESTING MATERIALS

The present invention relates to a device for testing materials in a non-destructive manner by means of ultrasound and eddy current. Heretofore it was known to conduct the eddy current and ultrasound testing by means of two separate testing devices and to carry out the testing operations one after the other. This heretofore known testing method has considerable disadvantages which consist in that, for instance, the pattern or shape of a tear discovered at the workpiece surface by an eddy current testing can be pursued further into the interior of the workpiece only when the eddy current testing device is removed from the tear and the ultrasound testing device is placed precisely at the same workpiece area.

Such a precise adjusting of the second testing device to the place of the first testing device is time consuming and awkward.

There has also become known a testing unit according to which both testing devices are arranged one adjacent to the other and in front of which the workpiece to be tested is moved. With this testing device it is necessary that the result of the testing of a workpiece area, when the latter has reached the first testing device, is stored in a storing device from which it is called off at the precise moment when the same workpiece area is being tested by the second testing device.

The precise calling-off of the test result requires a precise adjustment to the respective speed of the workpiece. The adjusting device as well as the intermediate storing device are relatively complicated devices, and furthermore the speed of the workpiece must always follow the same rectilinear direction. Very irregular or complicated testing paths, such as for instance arc-shaped or bent testing paths, cannot properly be tested.

It is therefore, an object of the present invention to design an eddy current and ultrasound testing device composed of a few simple structural elements by means of which the workpiece ranges of a large workpiece to be tested can be tested in quick succession by ultrasound and eddy current, while the testing can be carried out without being influenced even at varying speed and direction of the relative movement between workpiece and testing device.

This object and other objects and advantages of the invention will appear more clearly from the following specification in connection with the accompanying drawings, in which:

FIG. 1 diagrammatically illustrates the ultrasound and eddy current testing device which is centrally arranged with the testing coils.

Figure 2:
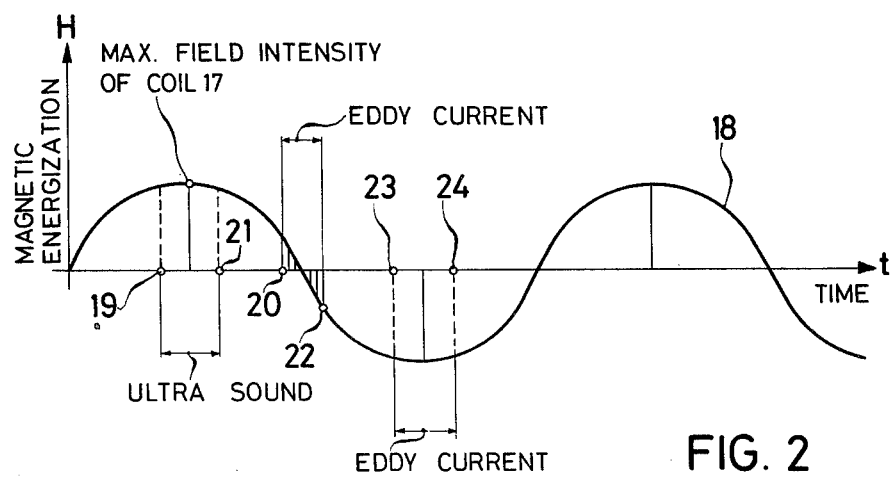

FIG. 2 shows by way of a diagram the operating periods of the ultrasound and eddy current testing device in conformity with the energization of the coils.

Figure 3:
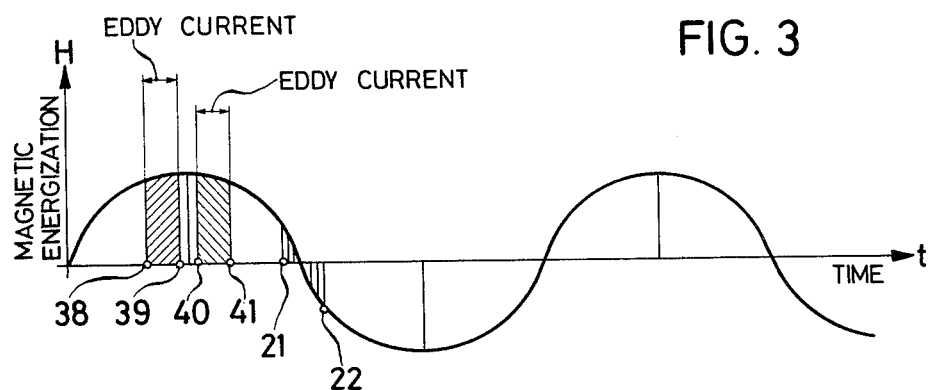

FIG. 3, likewise in the form of a diagram, shows the periods of operation in a different time sequence.

Figure 4:
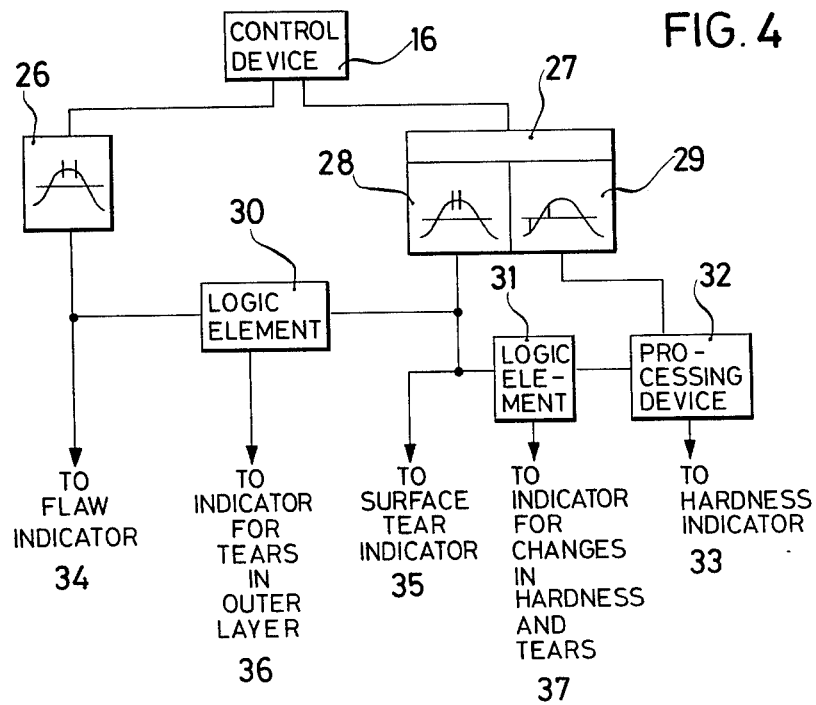

FIG. 4 is a block diagram of the evaluating device for the measured values.

The device according to the present invention is characterized primarily in that the ultrasound testing device operates in conformity with the electrodynamic converter principle and that the testing coils of both testing devices are arranged centrally with regard to each other in such a way that the workpiece ranges covered or controlled by the testing coils have a common or approximately common central axis and that a control device is provided which briefly turns-on and turns-off the ultrasound and eddy current testing devices.

The ultrasound testing device must work according to the electrodynamic converter principle because during the operation of other ultrasound testing devices coupling liquids are required which considerably interfere with the eddy current testing. The testing coils of both testing devices are located centrally with regard to each other so that the pattern or shape of a workpiece flaw can be followed from the surface to the interior of the workpiece and vice versa solely by alternately turning-on and turning-off the testing coils. According to the simplest embodiment of the invention, the alternating turning-on and turning-off of the testing coils is effected manually. Both testing devices from the very start test in the same region of the workpiece so that no adjusting operation is necessary. Instead of the testing coils, also in an analogous manner all of the testing devices or other parts thereof may be turned-on and turned-off. The purpose of the turning-off operations consists in preventing the testing pulses of both testing devices from superimposing upon each other and from influencing each other in the receiver.

According to an improved embodiment of the invention, the handling of the device as well as the recognizing of the workpiece flaws becomes particularly simply by providing a control device which briefly and alternately turns-on and turns-off the ultrasound and eddy current testing devices. When the alternate turning-on and turning-off steps follow each other very quickly, the advantage is obtained that, also with a relative movement between the testing coils and the workpiece, approximately the same workpiece range is tested by each coil. A quick alternating turning-on and turning-off is particularly advantageously effected by energizing the coil for the energization of the magnetic field of the electrodynamic converter by alternating current or by intermittent direct current and by connecting the control device for automatically alternately briefly turning-on and turning-off the ultrasound and eddy current testing devices to the coil for the energization of the magnetic field, while designing the control device in such a way that it will turn-on and turn-off in conformity with the magnitude of the energization of the magnetic field coil.

A very good possibility of recognizing flaws consists in so designing the control device for automatically alternately and briefly turning-on and turning-off the ultrasound and eddy current testing devices that, during the energization of the coil for magnetizing the electrodynamic converter, in the range of the maximum the ultrasound and the eddy current testing device are alternately turned-on and turned-off. When the ultrasound testing device is turned-on, interior flaws can be recognized, and when the eddy current device is turned-on, surface flaws will show up. When both testing devices simultaneously indicate a flaw, the conclusion can be drawn that the tear extends from the surface into the interior of the workpiece. The discovery of such flaws is particularly important because, for instance in rollers of a rolling mill, such flaws quickly result in the breaking of the outer layer of the rollers.

If only the eddy current testing device indicates a flaw, while the ultrasound testing device does not show any flaw, three possibilities exist, namely:

(1) a surface tear of slight depth, (2) a change in hardness,
(3) a combination of (1) and (2).

In order to be able to judge which of the three possibilities is present, the control device for alternately turning-on and turning-off the ultrasound and eddy current testing devices is so designed that also in the region of the zero points of the energizing of the coil the eddy current testing device is turned-on.

If also when testing with the eddy current testing device in the range of the zero points of the coil an indication is effected, this indicates a change in hardness in the workpiece.

With workpieces which move relative to the testing device, for instance on a roller train, the advancing speed is so adjusted to the turning-on and turning-off frequency of the ultrasound and eddy current testing devices that the workpiece ranges being tested at each testing interval will overlap to the major extent.

The testing coils can be favorably designed in such a way that the testing coil for the eddy current testing is arranged in the center of a circular testing coil employed for the ultrasound testing, the circular testing coil having a recessed inner portion. The testing coil for the eddy current may also consist of a portion of the testing coil for the ultrasound which in its inner part comprises a separate tap for the testing coil for the eddy current.

The centric arrangement of the testing coils may, however, also be realized in a different way. Thus, for instance, both testing coils may be made extremely flat and may be superimposed upon each other. In particular the testing coil for the eddy current may be made of a foil and, while placing between the two coils an insulating foil, may be cemented to or glued to the testing coil for generating the ultrasound field.

Inasmuch as some flaw indications are obtained only when the measured values of the ultrasound and eddy current testing devices are considered together and compaired, the device has connected thereto a measured value evaluating device which receives and processes the measured values of the ultrasound testing device and of the eddy current testing device which measures respectively with and without magnetic energization of the coil of the electrodynamic converter. This processing is effected by means of electric circuits known per se, as set forth in electronic literature listed further below.

Referring now to the drawings in detail, FIG. 1 shows an arrangement according to which the workpiece 11 is moved on a roller train 12, for instance in the direction of the arrow 13, in front of a testing coil 14 for ultrasound and the testing coil 15 for eddy current which is centrally arranged within the coil 14. The testing coils 14 and 15 are by means of the control device 16 alternately turned-on and turned-off in conformity with the energization of the coil 17 which serves for generating the necessary strong magnetic field necessary for operating the electrodynamic converter.

In FIG. 2 the approximately sine-shaped curve 18 represents the magnetic energization H of the coil 17 over the time t. The testing coil 14 for ultrasound is turned-on at the point 19 shortly prior to reaching the maximum field intensity of coil 17, and in point 20 is again turned-off. The testing coil 15 for eddy current is turned-on at the point 21 at a very low magnetic field intensity of coil 17 and is turned-off at the point 22. Furthermore, the testing coil 15 for eddy current is turned-on also at the point 23 at a very high magnetic field intensity of coil 17 and is again turned-off at the point 24.

A circuit according to which the testing coil 14 is turned-on at the point 23 and in which the testing coil 15 is turned-on at the point 19 is likewise possible with the same good results. The decisive point is that the magnetic field intensity of coil 17 is high. The polarity of the energization is immaterial. A testing cycle for testing a workpiece range thus extends over the time period which lies between the points 19 and 24 of the energization. In this relatively short time the workpiece 11 has, at the normal testing speeds, been displaced only slightly in front of the testing coils 14, 15, which means that the test result is almost the same as in the case when the workpiece 11 is stationary in front of the testing coils during the entire testing cycle. In the following periods of energization of coil 17 the testing cycle is repeated for successive workpiece ranges. The workpiece ranges to be tested overlap somewhat so that no untested areas remain on the workpiece 11. At high advancing speed of the workpiece 11 the frequency of the alternating current of 50 Hz does not suffice to allow a testing in the described manner. In such an instance the frequency of the current for energizing coil 17 must be increased in conformity with the high advancing speed of the workpiece 11.

The ultrasound and the eddy current testing which are within the range of the maximum of the energization of coil 17 may also be effected in a single half period according to FIG. 3. With this embodiment, the ultrasound testing starts at point 38 and ends at point 39 whereas the eddy current testing starts at point 40 and ends at point 41. A testing cycle with this embodiment lasts only from point 38 to point 22. Therefore, this embodiment is, when energizing coil 17 with alternating current, more suited for higher advancing speeds of the workpiece 11 than the above described embodiment of FIG. 2.

FIG. 4 shows by way of a block diagram the way of operation of the measured value processing device 25. This device receives its measured values from the control device 16 in conformity with the energization of coil 17.

In the individual functional units there is symbolically shown at what state of energization of coil 17 these functional units work.

The ultrasound testing device 26 receives the measured values from the testing coil 14 through the intervention of the control device 16 and conveys the measured values directly to the flaw indicator 34 for indicating interior flaws and to a logic element 30. The ultrasound testing device 26 always operates in the region of the maximum energization of coil 17.

The eddy current testing device 27 operates with its range 28 in the region of the maximum energization of coil 17 and furthermore operates with its range 29 in the region of the zero point of the energization. In the region of the maximum energization, the measured values are from point 28 conveyed directly to the surface tear indicator 35 and furthermore to the logical elements 30 and 31. The logic element 30 conveys an information to the indicator 36 for tears in the outer layer only when for the workpiece range to be tested also an inner flaw is present.

The measured values of the eddy current testing device 27 which are obtained during the very low energization of coil 17 in range 29 are conveyed to the processing device 32. In the processing device 32 a mean value is formed of the measured values of the workpiece ranges already tested, and the deviation of the measured value from the mean value is ascertained. When this deviation exceeds the magnitude of a previously introduced threshhold value, this information is conveyed to the indicator 33 for the change in hardness. Furthermore, the information is conveyed to the logic element 31 which, in case a surface tear is likewise present, turns-on the indicator 37 for changes in hardness and for indicating tears. Instead of the indicating devices 33–37, it is also possible to provide writing instruments.

The structural units contained in the measured value processing device or data logger 25 are generally known and, therefore, have not been explained in detail. Reference may be had to the Handbook "DIGITALE Electronik in der Messtechnik A und Datenverarabeitung" by Dokter und Steinhauer, Volume I, published by Philips Fachbucher 1969, especially pages 3–7 and 10–12. Further reference may be had to the Handbook by Richter Title "Impulspraxis in Schaltungen, Versuchen und Oszillogrammen" published by Telekosmos, Frankhsche Verlagshandlung, Stuttgart 1968. Concerning the control device 16, reference can be made to a book by Krautkramer, Werkstoffprufung mit Ultraschall, 3. Auflage, Springer-Verlag Berlin Heidelberg, New York 1975, on page 198, lines 5–8; also a book "Digitale Elektronik in der Messtechnik und Datenverarbeitung Bank I: "Theoretische Grundlangen und Schaltungstechnik" by F. Kokter and I Steinhauer, 1969, Philips Fachbucher published by Deutsche Philips GmbH-Hamburg (pages 170–175, especially page 171-FIGS. 4.15-1); also a book "Steuerungs- und Regelungstechnik, Band 2 by Werner Taeger (1964) in the "Franckh'schen Verlagshandlung Stuttgart, published by Heinz Richter (see pages 132–135, especially FIG. 61).

The functions of the measuring value processing device 25 referred to in connection with FIG. 4 may also be supplemented by additional devices. Additional devices are registering devices such as recorders or an aerograph or a spray gun for marking in colors the flaws, or a sorting device for different qualities of the workpiece.

It is, of course, to be understood that the present invention is by no means limited to the particular showing in the drawings but also comprises any modifications within the scope of the appended claims.

What we claim is:

1. An apparatus for non-destructively testing materials, which includes in combination: an ultra sound material testing device operating in accordance with the electro dynamic converter principle, and having a first testing coil provided therewith, an eddy current material testing device having a second testing coil provided therewith, said first and second testing coils being centrally arranged with regard to each other in such a way that the regions of effectiveness controlled by said testing coils have an at least approximately common central axis, and a control device including an additional energizing coil operable briefly and alternately to turn on and off the respective testing coil of said ultra sound and eddy current material testing devices.

2. An apparatus in combination according to claim 1, which includes an electric source and additional coil energized thereby for generating the magnetic field for operating said ultra sound material testing device.

3. An apparatus in combination according to claim 2, in which said control device is electrically connected to said first and second testing coils and is operable alternately to turn on and off said first and second testing coils in accordance with the energization of said additional coil.

4. An apparatus in combination according to claim 2, in which said additional coil is energizable by alternating current from said source.

5. An apparatus in combination according to claim 2, in which said additional coil is energizable by intermittent direct current from said source.

6. An apparatus in combination according to claim 2, in which said control device in response to the energization of said additional coil within the region of the maximum is operable alternately to turn on and off said ultra sound material testing device and said eddy current material testing device, respectively.

7. An apparatus in combination according to claim 2, in which said eddy current material testing device is in its turned on condition within the area in which the energization of said additional coil passes through zero.

8. An apparatus in combination according to claim 1, which includes supporting means operable to receive the workpiece to be tested and to premit a relative movement between said supporting means on one hand and said first and second coil and said additional coil on the other hand, the advancing speed of said relative movement being adjustable with regard to the turning on and turning off frequency of said ultra sound material testing device and said eddy current material testing device so that the workpiece regions tested during each testing period overlap each other.

9. An apparatus in combination according to claim 1, which includes a measured value processing device connected to said ultra sound and eddy current testing devices and operable to receive and process the measured values of the ultra sound material testing device, and of the eddy current testing device measuring with and without magnetic energization of said additional coil of said ultra sound material testing device.

* * * * *